United States Patent
Jagannathan et al.

(10) Patent No.: US 9,679,077 B2
(45) Date of Patent: Jun. 13, 2017

(54) AUTOMATED CLINICAL EVIDENCE SHEET WORKFLOW

(71) Applicant: MModal IP LLC, Franklin, TN (US)

(72) Inventors: Vasudevan Jagannathan, Morgantown, WV (US); Juergen Fritsch, Pittsburgh, PA (US)

(73) Assignee: MModal IP LLC, Franklin, TN (US)

( * ) Notice: Subject to any disclaimer, the term of this patent is extended or adjusted under 35 U.S.C. 154(b) by 462 days.

(21) Appl. No.: 13/928,776

(22) Filed: Jun. 27, 2013

(65) Prior Publication Data

US 2014/0006431 A1 Jan. 2, 2014

Related U.S. Application Data

(60) Provisional application No. 61/666,303, filed on Jun. 29, 2012.

(51) Int. Cl.
*G06F 17/30* (2006.01)
*G06Q 10/06* (2012.01)
(Continued)

(52) U.S. Cl.
CPC ...... *G06F 17/30943* (2013.01); *G06F 19/328* (2013.01); *G06Q 10/06* (2013.01); *G06Q 50/00* (2013.01); *G06Q 50/22* (2013.01)

(58) Field of Classification Search
CPC ............................................. G06F 17/30943
(Continued)

(56) References Cited

U.S. PATENT DOCUMENTS

| 5,148,366 A | 9/1992 | Buchanan |
|---|---|---|
| 6,377,922 B2 | 4/2002 | Brown |

(Continued)

FOREIGN PATENT DOCUMENTS

| JP | 2011118538 A | 6/2011 |
|---|---|---|
| WO | 2011100474 A2 | 8/2011 |
| WO | 2011100474 A3 | 1/2012 |

OTHER PUBLICATIONS

Huser, Vojtech, et al., "Use of Workflow Technology Tools to Analyze Medical Data", CBMS '06, Salt Lake City, UT, Jun. 22-23, 2006, pp. 455-460.*

(Continued)

*Primary Examiner* — R. Stevens
(74) *Attorney, Agent, or Firm* — Blueshift IP, LLC; Robert Plotkin

(57) ABSTRACT

Embodiments of the present invention are directed to computer systems for implementing dynamic, data-driven workflows within healthcare and other environments. Such a system may include a computer-processable definition of one or more workflows. Each workflow definition may define various aspects of the corresponding workflow, such as the data required by the workflow, a process for extracting such data from a variety of structured and/or unstructured data sources, a set of process steps to be performed within the workflow, and a condition for triggering the workflow. The system may use the workflow definition to extract the data required by the workflow and to perform the workflow's process steps on the extracted data in response to determining that the workflow's trigger condition has been satisfied. The workflow may change in response to changes in data extracted by the workflow.

12 Claims, 2 Drawing Sheets

(51) Int. Cl.
  *G06Q 50/00* (2012.01)
  *G06Q 50/22* (2012.01)
  *G06F 19/00* (2011.01)

(58) Field of Classification Search
  USPC .......................................................... 707/755
  See application file for complete search history.

(56) References Cited

U.S. PATENT DOCUMENTS

| | | | |
|---|---|---|---|
| 7,379,946 | B2 | 5/2008 | Carus |
| 7,447,988 | B2* | 11/2008 | Ross ............................ 715/221 |
| 7,584,103 | B2* | 9/2009 | Fritsch et al. ................ 704/257 |
| 7,613,610 | B1 | 11/2009 | Zimmerman |
| 7,716,040 | B2* | 5/2010 | Koll et al. ........................ 704/9 |
| 7,797,172 | B2* | 9/2010 | Fitzgerald et al. ............. 705/4 |
| 7,869,998 | B1 | 1/2011 | DiFabbrizio |
| 8,024,196 | B1 | 9/2011 | Wodtke |
| 8,583,439 | B1 | 11/2013 | Kondziela |
| 8,805,703 | B2* | 8/2014 | Martin et al. ..................... 705/3 |
| 8,862,483 | B2* | 10/2014 | Scarola .................. G06Q 10/06 705/2 |
| 2002/0077819 | A1 | 6/2002 | Girardo |
| 2003/0083915 | A1 | 5/2003 | Guicciardi |
| 2003/0204588 | A1 | 10/2003 | Peebles et al. |
| 2004/0044546 | A1 | 3/2004 | Moore |
| 2004/0078236 | A1 | 4/2004 | Stoodley |
| 2004/0220843 | A1 | 11/2004 | Walter |
| 2004/0243545 | A1* | 12/2004 | Boone et al. ..................... 707/2 |
| 2004/0254816 | A1 | 12/2004 | Myers |
| 2005/0071194 | A1 | 3/2005 | Bormann |
| 2005/0137910 | A1* | 6/2005 | Rao et al. ......................... 705/3 |
| 2005/0158767 | A1 | 7/2005 | Haskell |
| 2006/0020493 | A1* | 1/2006 | Cousineau et al. ............. 705/2 |
| 2006/0031194 | A1 | 2/2006 | Ghazaleh |
| 2006/0047539 | A1 | 3/2006 | Huang |
| 2006/0122865 | A1 | 6/2006 | Preiss |
| 2007/0011134 | A1 | 1/2007 | Langseth |
| 2007/0027778 | A1* | 2/2007 | Schellhammer ....... G06Q 10/10 705/26.1 |
| 2007/0033073 | A1* | 2/2007 | Tajaliawal et al. ............. 705/3 |
| 2007/0106751 | A1 | 5/2007 | Moore |
| 2007/0118401 | A1 | 5/2007 | Mahesh et al. |
| 2007/0118410 | A1 | 5/2007 | Nadai |
| 2007/0143164 | A1* | 6/2007 | Kaila et al. ....................... 705/8 |
| 2007/0192143 | A1 | 8/2007 | Krishnan |
| 2007/0198907 | A1 | 8/2007 | Degala |
| 2007/0203708 | A1 | 8/2007 | Polcyn |
| 2007/0239499 | A1 | 10/2007 | Shukla et al. |
| 2008/0077451 | A1 | 3/2008 | Anthony |
| 2008/0141072 | A1 | 6/2008 | Kalgren et al. |
| 2008/0147453 | A1 | 6/2008 | Kogan |
| 2008/0275729 | A1* | 11/2008 | Taggart et al. .................. 705/2 |
| 2009/0006156 | A1 | 1/2009 | Hunt |
| 2009/0048833 | A1 | 2/2009 | Fritsch |
| 2009/0089092 | A1 | 4/2009 | Johnson et al. |
| 2009/0089100 | A1* | 4/2009 | Nenov et al. ..................... 705/3 |
| 2009/0182580 | A1* | 7/2009 | Martin et al. ..................... 705/3 |
| 2010/0070291 | A1 | 3/2010 | Handy |
| 2010/0094657 | A1 | 4/2010 | Stern |
| 2010/0125450 | A1 | 5/2010 | Michaelangelo |
| 2010/0138241 | A1* | 6/2010 | Ruark et al. ..................... 705/3 |
| 2010/0145720 | A1* | 6/2010 | Reiner ............................. 705/2 |
| 2010/0217624 | A1 | 8/2010 | Kay |
| 2010/0250236 | A1 | 9/2010 | Jagannathan |
| 2010/0305997 | A1 | 12/2010 | Ananian |
| 2011/0093293 | A1 | 4/2011 | G. N. |
| 2011/0173153 | A1 | 7/2011 | Domashchenko |
| 2011/0295616 | A1* | 12/2011 | Vesto ..................... G06F 3/0486 705/3 |
| 2012/0041950 | A1* | 2/2012 | Koll et al. ..................... 707/728 |
| 2012/0065987 | A1 | 3/2012 | Farooq |
| 2012/0166220 | A1* | 6/2012 | Baldwin et al. .................. 705/3 |
| 2012/0173255 | A1* | 7/2012 | Korhnak ................ G06Q 10/06 705/2 |
| 2012/0215782 | A1 | 8/2012 | Jagannathan |
| 2012/0221589 | A1 | 8/2012 | Shahar |
| 2012/0323572 | A1 | 12/2012 | Koll |
| 2012/0323598 | A1 | 12/2012 | Koll |
| 2013/0144907 | A1* | 6/2013 | White ................... G06F 19/321 707/776 |
| 2013/0191136 | A1* | 7/2013 | Apshago ................ G06Q 10/10 705/2 |
| 2015/0310362 | A1 | 10/2015 | Huffman |

OTHER PUBLICATIONS

Luo, Zongwei, et al., "Exception Handling in Workflow Systems", Applied Intelligence, vol. 13, Issue 2, Sep. 2000, pp. 125-147.*
Curia, Rosario, et al., "Knowledge Management in Health Care: an Architectural Framework for Clinical Process Management Systems", DEXA '05, IEEE Computer Society, © 2005, 5 pages.*
Egan, Marie, "Clinical Dashboards—Impact on Workflow, Care Quality and Patient Safety", Crt Care Nurs Q, vol. 29, No. 4, Lippincott Williams & Williams, © 2006, pp. 354-361.*
Stead, William W., et al., "Integration and Beyond: Linking Information from Disparate Sources and into Workflow", Journal of American Medical Informatics Assn, vol. 7, No. 2, Mar./Apr. 2000, pp. 135-145.*
Grimson, Jane, "Delivering the electronic healthcare record for the 21st century", International Journal of Medical Informatics, vol. 64, Issues 2-3, Dec. 2001, pp. 111-127.*
Wilcox, Lauren, et al., "Physician-Driven Management of Patient Progress Notes in an Intensive Care Unit", CHI 2010, Atlanta, GA, Apr. 10-15, 2010, pp. 1879-1888.*
Schnipper, Jeffrey L., et al., "Smart Forms in an Electronic Medical Record: Documentation-based Clinical Decision Support to Improve Disease Management", Journal of American Medical Informatics Assn, vol. 15, No. 4, Jul./Aug. 2008, pp. 513-523.*
Hanson, Diane, "Chap 15: Evidence-Based Clinical Decision Support", Nursing Informatics, Springer-Verlag, London, © 2011, pp. 243-258.*
Zou, Qinghua, et al., "IndexFinder: A Method of Extracting Key Concepts from Clinical Texts for Indexing", AMIA 2003 Symposium Proceedings, © 2003, pp. 763-767.*
Rowland, A. L., et al., "Information eXtraction from Images (IXI): Image Processing Workflows Using a Grid Enabled Image Database", Proc. Of DiDaMIC, vol. 4, © 2004, pp. 55-64.*
"Applying Systems Engineering Principles in Improving Health Care Delivery," Kopach-Konrad et al., Journal of General Internal Medicine, Dec. 2007, vol. 22, Issue 3 Supplement, pp. 431-437.

* cited by examiner

AUTOMATED CLINICAL EVIDENCE SHEET WORKFLOW

CROSS-REFERENCE TO RELATED APPLICATIONS

This application claims the benefit of U.S. Prov. Pat. App. Ser. No. 61/666,303, filed on Jun. 29, 2012, entitled, "Automated Clinical Evidence Sheet Workflow," which is hereby incorporated by reference herein.

BACKGROUND

Many workflows in the healthcare industry (and other industries) require information to be extracted from a variety of data sources and for the extracted information to be used within the workflow according to the particular nature of the workflow. As one example, consider a patient who has undergone surgery at a hospital. After the surgery has been completed, the hospital must generate a bill for all of the services provided and materials used by the hospital in connection with the surgery, including pre- and post-surgical care. Generating such a bill may require obtaining information from a variety of data sources, such as transcripts of notes dictated by the surgeon (possibly before, during, and after the surgery); typewritten notes typed by the surgeon, nurses, anesthesiologist, and other medical personnel; and data stored within an Electronic Health Record (EHR) that stores a variety of information about the patient. For example, if the bill is to be sent to the patient it may be necessary to extract from such data sources information about the kind of surgery performed; the number of doctors; nurses, and other personnel who participated in the surgery; the equipment that was used in the surgery; the materials that were used to perform the surgery; the amount of time the patient stayed in the hospital after the surgery; and the medications that were prescribed to the patient as a result of the surgery. If the bill is to be sent to an insurer, then the hospital may need to provide information specified by a standard mapping referred to as a Diagnostic Related Grouping (DRG). DRGs represent standardized payment structures, such as a specific amount to be paid to the hospital for a particular type of surgery.

Extracting such a wide variety of information from such a wide variety and large number of sources can be difficult, time-consuming, and prone to error.

SUMMARY

Embodiments of the present invention are directed to computer systems for implementing dynamic, data-driven workflows within healthcare and other environments. Such a system may include a computer-processable definition of one or more workflows. Each workflow definition may define various aspects of the corresponding workflow, such as the data required by the workflow, a process for extracting such data from a variety of structured and/or unstructured data sources, a set of process steps to be performed within the workflow, and a condition for triggering the workflow. The system may use the workflow definition to extract the data required by the workflow and to perform the workflow's process steps on the extracted data in response to determining that the workflow's trigger condition has been satisfied. The workflow may change in response to changes in data extracted by the workflow.

For example, one embodiment of the present invention is directed to a method performed by at least one computer processor, the method comprising: (A) determining that a trigger condition defined by a trigger condition definition of a workflow definition has been satisfied; (B) in response to the determination in (A): (B)(1) using a process defined by a data extraction process definition associated with the workflow definition to extract, from at least one data source, data defined by a data definition associated with the workflow definition; (B)(2) storing the extracted data in an evidence sheet; and (B)(3) applying, to the extracted data, steps defined by a workflow process definition associated with the workflow definition to generate first workflow output.

Other features and advantages of various aspects and embodiments of the present invention will become apparent from the following description and from the claims.

DETAILED DESCRIPTION

Figure 1:
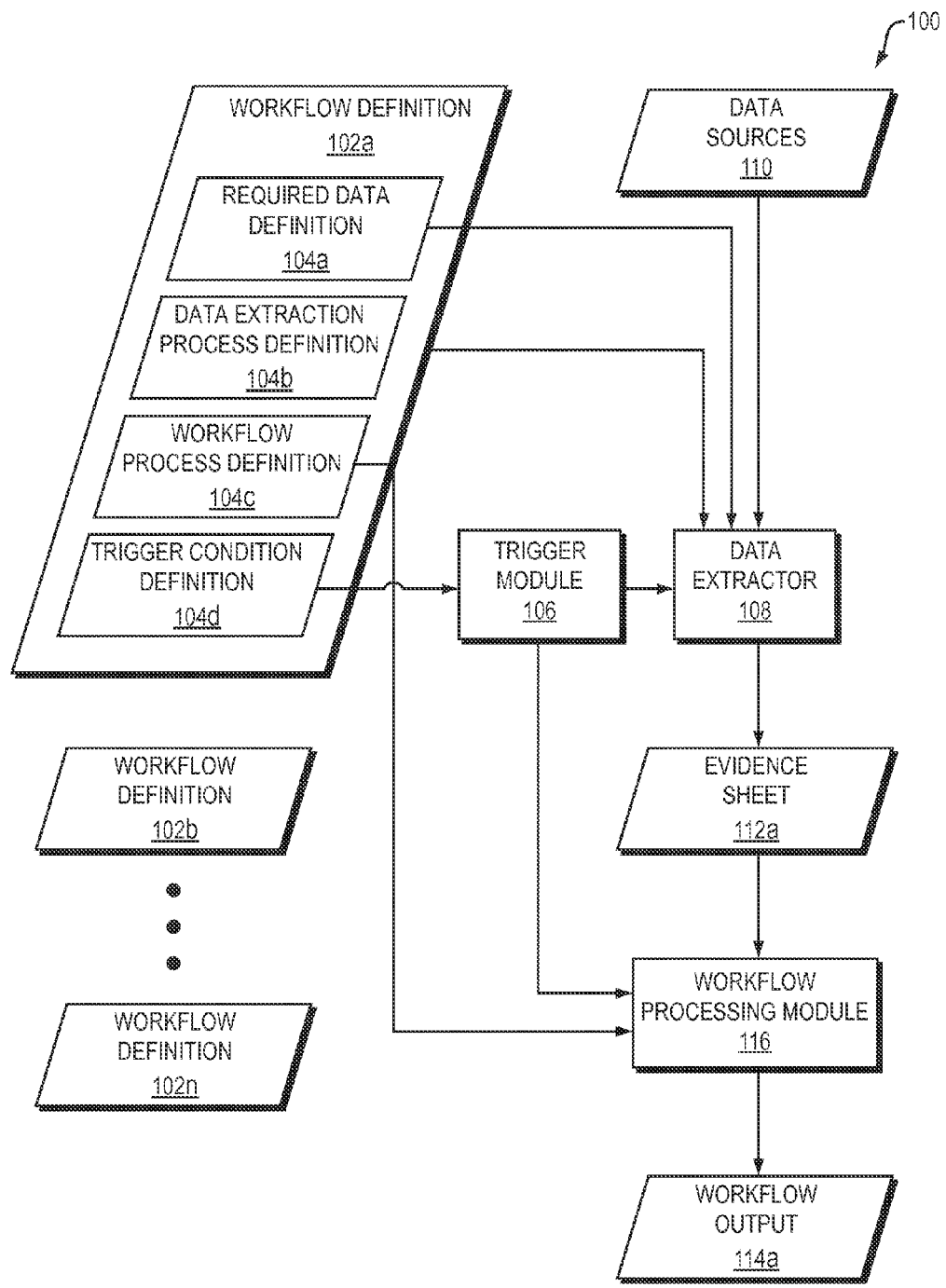
FIG. 1 is a dataflow diagram of a workflow automation system according to one embodiment of the present invention.

One of the reasons for the difficulty of extracting information from a wide variety and large number of sources is that the data sources may take a variety of forms. For example, some data sources, such as EHRs, may take the form of structured data, in which data are stored in discrete fields, such as "Surgery Type," "Surgery Date," and "Current Medications." It may be easier to extract information from such structured data sources than from unstructured data sources (such as freeform doctors' notes) because structured data has already been stored in a form that can be understood by a computer. One difficulty with structured data sources, however, is that structured data may not be stored in a form that is most suitable for generating a bill. For example, the length of the patient's stay after the surgery may not be stored directly in the patient's EHR. Instead, as a very simple example, the patient's arrival date and departure date may be stored in the patient's EHR, in which case it may be necessary to calculate the duration of the patient's stay by subtracting the arrival date from the departure date. As another example, the patient's birth date but not the person's age may be stored in the patient's EHR, in which case obtaining the patient's age may require subtracting the person's birth date from the current date. As yet another example, the amount of medication provided to the patient may need to be calculated from multiple records, each of which represents a particular amount of medication provided to the patient. In practice, much more complex processing may need to be performed on existing structured data to process that data within a particular workflow, such as a workflow for generating a bill. The purpose of this example is merely to illustrate that even when the meaning of structured data may be readily understood by a computer, existing discrete data elements may still need to be combined with each other and processed in other ways to satisfy the requirements of a particular workflow.

Some data sources, such as a doctor's typewritten or transcribed notes, may take the form of unstructured data, such as freeform text written in English or another natural language. It may therefore be particularly difficult to extract data from such sources in a form that may be used to generate a bill or perform other workflows. It may be necessary first to apply Natural Language Processing (NLP) and/or other processing on such unstructured data to generate structured data that may be used to generate a bill or perform another workflow. Examples of techniques that may be used to extract structured data from transcribed documents may be found, for example, in U.S. Pat. No. 7,584,103, issued on Sep. 1, 2009, entitled, "Automated Extraction of Semantic Content and Generation of a Structured Document from Speech," and U.S. Pat. No. 7,716,040, issued on May 11, 2010, entitled, "Verification of Extracted Data."

The process of generating a bill based on structured and/or unstructured medical data is merely one example of a workflow that may be performed in the healthcare industry. A wide variety of healthcare workflows involve processes that must extract and analyze data stored in a wide variety of sources.

Figure 2:
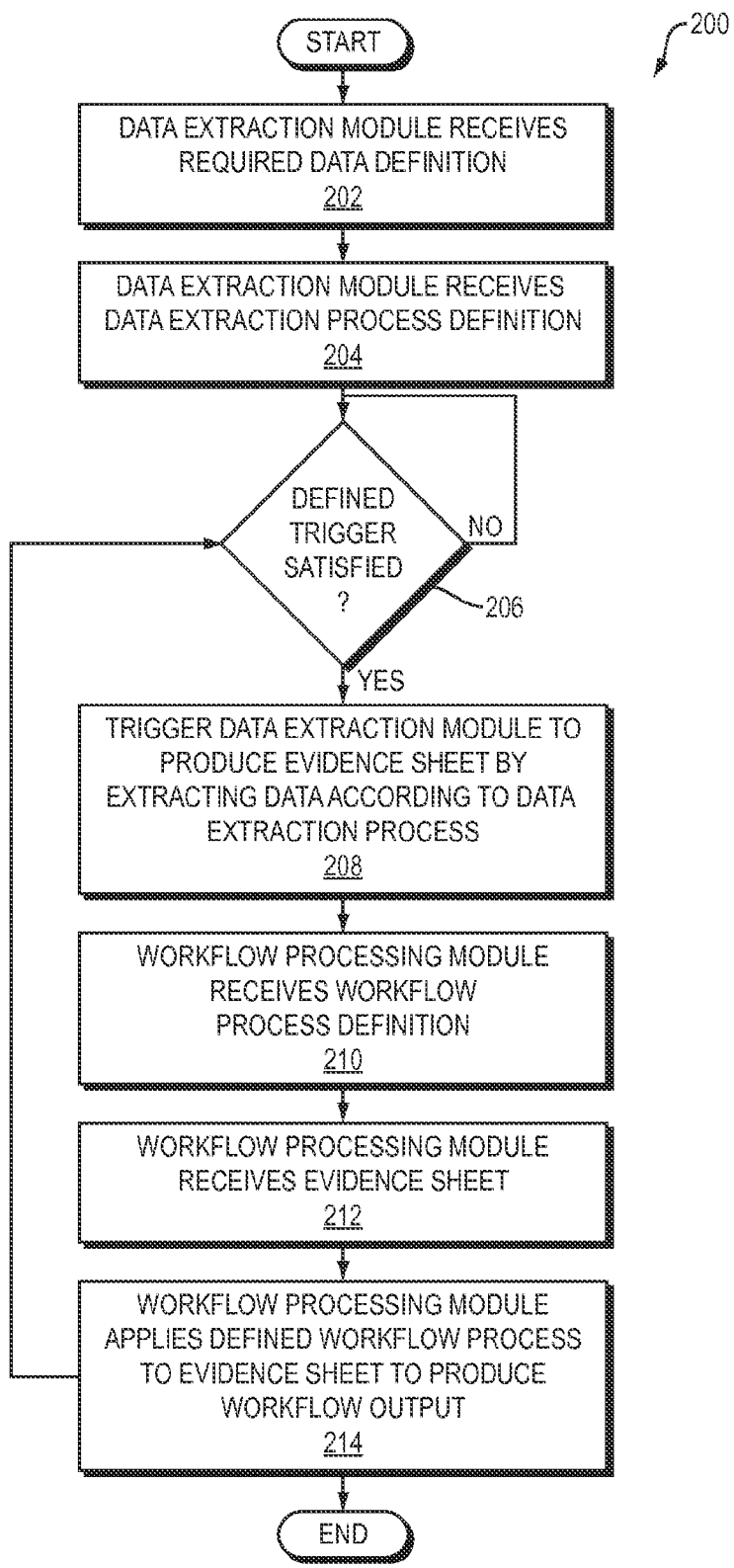
FIG. 2 is a flowchart of a method performed by the system of FIG. 1 according to one embodiment of the present invention.

Embodiments of the present invention are directed to systems for systematizing and automation workflows, such as the healthcare workflows described above. For example, embodiments of the present invention may be used to generate, store, and process one or more computer-readable workflow definitions, each of which defines a corresponding workflow. Referring to FIG. 1, a dataflow diagram is shown of a workflow automation system 100 according to one embodiment of the present invention. Referring to FIG. 2, a flowchart is shown of a method 200 that is performed by the system 100 of FIG. 1 according to one embodiment of the present invention.

The workflow automation system 100 of FIG. 1 includes a plurality of workflow definitions 102a-n, where n may be any number. Each of the workflow definitions 102a-n defines a corresponding workflow. In other words, workflow definition 102a defines a first workflow, workflow, definition 102b defines a second workflow, and definition 102n defines an nth workflow in a plurality of workflows.

A workflow definition may, for example, include:

A required data definition, which defines the data that are required by the corresponding workflow. In the example of a surgery bill generation workflow, the required data definition may, for example, specify that the surgery bill generation workflow requires data representing the type of surgery, the number of doctors involved in the surgery, and the length of the patient's stay, among other data. A required data definition may define the corresponding required data in any of a variety of ways, such as by reference to any one or more of the following: keywords, codes, database field names, and formulas. A required data definition may define any number of units of data drawn from any number of sources (e.g., one, two, or more sources), and from any combination of unstructured and structured data sources.

A data extraction process definition, which defines a process for extracting (e.g., from one or more structured and/or unstructured data sources) the data defined by the corresponding required data definition. In the example of a surgery bill generation workflow, the data extraction process definition may, for example, indicate that the type of the surgery is to be extracted from a "Surgery Type" field of the patient's EHR record, and that the medications prescribed to the patient are to be extracted from the physician's notes that were dictated after the surgery. The result of performing the data extraction process defined by a data extraction process definition is a set of data that is referred to herein as an "evidence sheet." Although the required data definition and data extraction process definition may be implemented as distinct definitions, alternatively the required data definition and the data extraction process definition may be integrated with each other in a variety of ways. For example, the data extraction process definition may be implicit in the required data definition.

A workflow process definition, which defines a set of steps to be performed on the evidence sheet data extracted by the corresponding data extraction process, and thereby to generate workflow output (e.g., a bill). The workflow process definition may assign each step to a specified actor or actors, and different steps in the workflow process may be assigned to different actors. In the example of a surgery bill generation workflow, a step of reviewing the extracted data may be assigned to one person and a be assigned to a different person.

A trigger condition definition 104d, which defines a condition under which steps in the corresponding workflow need to be undertaken. For example, the completion of a surgery may be a trigger condition that triggers the initiation of a surgery bill generation workflow. Examples of kinds of data that may satisfy a trigger condition include, for example, data relating to the following properties of the patient's and/or the medical care received by the patient: demographics, patient characteristics, symptoms, diagnostics, medications, devices, procedures, labs, and vitals. A trigger condition may, for example, be implemented as a rule that is applied to any combination of such data.

Although the workflow definition 102a is shown in FIG. 1 as containing the required data definition 104a, the data extraction process definition 104b, the workflow process definition 104c, and the trigger condition definition 104d, the workflow definition 102a may be associated with the data 104a-d in other ways. For example, the workflow definition 102a may contain a pointer to any one or more of the data 104a-d. Whether the data 104a-d are contained within the workflow definition 102a, pointed to (i.e., referenced by) the workflow definition 102a, or a combination thereof, the data 104a-d are said herein to be "associated with" the workflow definition 102a.

Referring again to FIG. 1, the workflow definition 102a, which defines a particular corresponding workflow, may include required data definition 104a, data extraction process definition 104b, workflow process definition 104c, and trigger condition definition 104d. Required data definition 104a defines the data that are required by the workflow defined by workflow definition 102a. Data extraction process definition 104b defines a process for extracting the data defined by the corresponding required data definition 104a. The workflow definition 102a further includes a workflow process definition 104c, which defines a set of steps to be performed on the data in the evidence sheet 110a. The workflow definition 102a further includes a trigger condition definition 104d, which defines a condition, the satisfaction of which causes the data extraction process defined by the data extraction process definition 104b to be performed to generate the evidence sheet 110a, which in turn causes the workflow process defined by the workflow process definition 104c to be applied to the evidence sheet 110a to produce workflow output 114a.

As a particular example of how the system 100 of FIG. 1 may operate, consider the following description of how the system 100 may be applied to the workflow definition 102a. It should be understood that the same process may be applied to the other workflow definitions 102b-n. The system 100 may include a data extraction module 108, which may receive as input the required data definition 104a (FIG. 2, operation 202) and the data extraction process definition 104b (FIG. 2, operation 204).

The system 100 may include a trigger module 106, which may receive the trigger condition definition 104d as input. The trigger module 106 may determine whether the trigger defined by the trigger condition definition 104d is satisfied (FIG. 2, operation 206). In response to determining that the trigger defined by the trigger condition definition 104d has been satisfied, the trigger module 106 may cause the data extraction module 108 to perform the data extraction process defined by data extraction process definition 104b, thereby extracting data from one or more data sources 110 (which may include structured data sources and/or unstructured data sources) to produce an evidence sheet 112a containing data required by the workflow defined by the workflow definition 102a (FIG. 2, operation 208). The data sources 110 may include, for example, any one or more of the following: clinical notes, doctors/nurses notes, medication admission records, lab results, structured documents (e.g., CCD documents), EHR records, diagnostic imaging reports, pathology reports, anesthesiology reports, cardiology reports, radiology reports, nephrology reports, neurology reports, and any other discipline-centric reports.

The data extraction module 108 may be a fully-automated module, such as a module implemented in hardware and/or software which performs the functions disclosed herein automatically (i.e., without human intervention). The functions disclosed herein as being performed by the data extraction module 108 may, however, be performed partially or solely manually. For example, a human operator may manually create the evidence sheet 112a, based upon inspection of the data sources 110 and a manual determination that the data sources 110 are deficient in some way. In such a case, the human operator may indicate the nature of the deficiency (e.g., that a particular type of data relating to a particular patient encounter is missing from the data sources) in the evidence sheet 112a. Any of the techniques disclosed herein may be performed in connection with such a manually-generated evidence sheet. One benefit of generating an evidence sheet manually is that doing so enables the human operator to take advantages of the workflow that is performed on the evidence sheet 112a by the workflow processing module 116.

The extraction process defined by the data extraction process definition 104b and performed by the data extraction module 108 may involve abstracting from some or all of the extracted data. As a result, the evidence sheet 112a may not include all of the data extracted by the data extraction module 108 from the data sources 110. Rather, the evidence sheet 112a may include abstracted data that the data extraction module 108 has produced by abstracting from the data sources 110. For example, consider a case in which a particular hospitalization involves a patient who has pneumonia. Data in the data sources 110 that relates to the patient's hospitalization may include a large number of instances of the word "pneumonia" and other data that refers to the patient's pneumonia. The data extraction module 108 may abstract from this large number of instances of the concept of "pneumonia" and include, in the evidence sheet 112a, only one or a small number of indications that the patient has pneumonia. The system 100 may allow users of the system 100 to view all of the extracted data that justifies the conclusion that the patient has pneumonia if such users choose to view such evidence.

The system 100 may further include a workflow processing module 116, which may receive as input the workflow process definition 104c (FIG. 2, operation 210) and the evidence sheet 112a (FIG. 2, operation 212). In response to determining that the trigger defined by the trigger condition definition 104d has been satisfied, the trigger module 106 may cause the workflow processing module 116 to apply the workflow process defined by the workflow process definition 104c to the data in the evidence sheet 112a, thereby producing workflow output 114a (e.g., a bill) (FIG. 2, operation 214). The method 200 may return to operation 206 automatically so that the workflow continues to operate repeatedly (e.g., continuously).

The act of applying the workflow process defined by the workflow process definition 104c may involve the workflow processing module 116 performing one or more steps in the workflow process automatically. Additionally or alternatively, however, one or more steps in the workflow may be associated with a corresponding human agent. To process a particular step in the workflow process, the workflow processing module 116 may interact with the human agent to whom the workflow step is assigned. For example, processing a particular workflow step assigned to a billing coder may involve presenting output representing certain specified information from the evidence sheet 112a to the billing coder and receiving input from the billing coder in response to the information from the evidence sheet 112a (such as a billing code or confirmation of a billing code).

Workflows may be static or dynamic. For example, the workflow process definition 104c may define a workflow process that includes a fixed set of steps that are performed by the workflow process defined by the workflow process definition 104c is performed. Alternatively, however, the workflow process definition 104c may define a workflow process that is dynamic, i.e., that includes steps that may change in response to inputs, such as data in the evidence sheet 112a. For example, in a "document deficiency" workflow, the introduction of a new document might cause a step to be added to the workflow according to which a different person is assigned to address a document deficiency that is evidenced by the introduction of the new document.

Furthermore, although the data extraction module 108 is described above as executing the data extraction process a single time to extract the required data from the data sources 110, this is merely an example and does not constitute a limitation of the present invention. Alternatively, for example, the data extraction module 108 may repeatedly (e.g., continuously) extract data from the data sources 110 to repeatedly (e.g., continuously) update the evidence sheet 112a in response to changes (e.g., additions, deletions, or modifications) to the data in the data sources 110. Similarly, the workflow processing module 116 may operate on the evidence sheet 112a as the data in the evidence sheet 112a changes. The workflow processing module 116 may, in other words, perform the workflow process defined by the workflow process definition 104c in a way that is responsive to changes in the data sources 110, as reflected by changes in the evidence sheet 112a. As a result, the workflow processing module 116 may implement dynamic, data-driven workflows.

Furthermore, although FIG. 1 shows only a single evidence sheet 112a, the system 100 of FIG. 1 may generate and/or operate on any number of evidence sheets using the techniques disclosed herein. For example, the data extraction module 108 may use workflow definition 102a to generate evidence sheet 112a, use workflow definition 102b to generate a second evidence sheet (not shown), and use workflow definition 102n to generate an nth evidence sheet (not shown).

Embodiments of the present invention may optimize data within an evidence sheet and/or across multiple sheets. For example, embodiments of the present invention may combine multiple evidence sheets to produce a single evidence sheet containing some or all of the data originally stored in the multiple evidence sheets. For example, if multiple evidence sheets contain data relating to a particular patient encounter, then some or all of the data from the multiple evidence sheets may be combined with each other, such as by combining all of the multiple evidence sheets to produce a single evidence sheet. For example, if a first evidence sheet contains evidence that is related to a heart failure document deficiency workflow, and a second evidence sheet contains evidence that is related to a heart failure quality measure workflow, then such evidence sheets may be combined with each other, in response to determining that both such evidence sheets related to a patient encounter involving heart failure. The resulting combined evidence sheet may still be used to drive multiple workflows (such as the heart failure document deficiency workflow and the heart failure quality measure workflow described above). For example, when the two evidence sheets are combined together, the data from each source evidence sheet may be tagged or otherwise associated with data specifying the workflow that is associated with that data, so that the data from the two source evidence sheets may continue to be used to drive the two workflows associated with those evidence sheets even though the evidence sheets have been combined together.

Once multiple evidence sheets have been combined, the workflows associated with those evidence sheets may also be combined. For example, if an evidence sheet containing evidence of a patient's pneumonia is combined with an evidence sheet containing evidence of the same patient's heart failure, then the document deficiency workflows associated with both such evidence sheets may be combined into a single workflow. As a result, when the combined workflow is executed, it is applied to the data in the combined evidence sheet. Such an embodiment enables an organization to address all document deficiencies related to a single patient at the same time (i.e., as part of the same workflow).

Consider a case in which the evidence sheet 112*a* is designed to support a Clinical Documentation Improvement (CDI) workflow. Such an evidence sheet 112*a* may contain evidence pointing to deficiencies in the existing documentation (in the data sources 110). The workflow processing module 116 may execute the workflow process defined by the workflow process definition 104*c* concurrently with the patient's treatment in the hospital. As a result, new documentation related to the patient may be created and added to the data sources 110 while the workflow processing module is executing the CDI workflow. Any piece of documentation that is added to the data sources 110 may cause new deficiencies to be identified within the evidence sheet 112*a* (e.g., by the workflow processing module 116). The identification of such a deficiency may in turn trigger the execution of a workflow by the workflow processing module 116, in which a case worker is assigned to investigate and correct the deficiency. Subsequently, further new documentation may be added to the data sources 110 which eliminates the previously-identified deficiency. In response, the data extraction module 108 may update the evidence sheet 112*a* to reflect that the deficiency has been eliminated. In response to this update of the evidence sheet 112*a*, the workflow processing module 116 may cancel the investigation of the deficiency that was previously initiated in response to identification of the deficiency.

Although only the contents of workflow definition 102*a* are shown in FIG. 1 for ease of illustration, other workflow definitions, such as workflow definitions 102*b* and 102*n*, may have the same or similar structure as workflow definition 102*a*. The contents of the other workflow definitions (such as workflow definitions 102*b* and 102*n*) may, however, differ from the contents of workflow definition 102*a*. For example:

workflow definition 102*b* may include a required data definition that defines different data than the required data definition 104*a* of workflow definition 102*a*;

workflow definition 102*b* may include a data extraction process definition that defines a different data extraction process than the data extraction process definition 104*b* of workflow definition 102*a*;

workflow definition 102*b* may include a workflow process definition that defines a different workflow process than the workflow process definition 104*c* of workflow definition 102*a*; and workflow definition 102*b* may include a trigger condition definition that defines a different trigger condition than the trigger condition definition 104*d* of workflow definition 102*a*.

Certain examples described above refer to a workflow for generating a bill for a surgery. This is merely one example of a workflow and does not constitute a limitation of the present invention. More generally, embodiments of the present invention may apply to any of a variety of workflows.

Another example of a workflow that may be implemented using embodiments of the present invention is a quality measure workflow. For example, if a patient is admitted to a hospital with a heart attack, then a quality measure workflow may specify that the following information should be extracted from data sources relevant to the patient: medications that were prescribed during the patient's stay; medications that were prescribed on discharge of the patient; lab results that are specific to heart conditions; and any counseling given to the patient related to smoking. The quality measure workflow may also specify certain process steps that should be applied to the extracted information to determine whether proper care was given to the patient.

Another example of a workflow that may be implemented using embodiments of the present invention is a clinical documentation improvement workflow. For example, if a patient's condition indicates that the patient has suffered a heart failure, then a clinical documentation improvement workflow may specify that the evidence that the physician relied upon to diagnose the patient with heart failure should be extracted from the data sources specified by the physician; that the extracted evidence should be analyzed to determine whether it justifies the conclusion that the patient has suffered a heart failure; and that if the evidence relied upon by the physician does provide sufficient support for the conclusion that the patient has suffered a heart failure, then the following information should be extracted from all available data sources: lab results that indicate heart failure, medications that are indicative of treatment provided for heart failure, and symptoms and diagnoses related to heart failure. This additional extracted data may then be analyzed and used to improve the physician's documentation of the patient's heart failure condition, by supplementing the documentation with additional information about evidence of the patient's heart failure.

Embodiments of the present invention have a variety of advantages. For example, in general, embodiments of the present invention enable data to be extracted automatically from a wide variety of sources, including both structured and unstructured sources, for use within medical workflows. Embodiments of the present invention provide a systematic and simple way to specify which information should be extracted automatically for use in a particular workflow, and the processes to be applied automatically to analyze the extracted data within the workflow. Embodiments of the present invention are particularly useful for automatically extracting information that is buried within freeform text documents, which are typically stored as word processing documents and which therefore are not otherwise readily processable by computer software. In other words, embodiments of the present invention make it possible to use a computer to automatically extract, from unstructured data sources, data which otherwise would need to be extracted manually and tediously from such sources. Furthermore, embodiments of the present invention enable such extracted information (whether such information was extracted automatically or manually) to be processed automatically or semi-automatically as part of a workflow that is defined in association with the extracted data.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Each computer program within the scope of the claims below may be implemented in any programming language, such as assembly language, machine language, a high-level procedural programming language, or an object-oriented programming language, functional programming language or any other higher level language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Such data include, but are not limited to, the workflow definitions 102, data sources 110, evidence sheet 112a, and workflow output 114a. Embodiments of the invention may store such data in such data structure(s) and read such data from such data structure(s).

What is claimed is:

1. A method performed by at least one computer processor, the method comprising:
   (A) determining that a trigger condition defined by a trigger condition definition of a workflow definition has been satisfied;
   (B) in response to the determination in (A):
      (B)(1) using a process defined by a data extraction process definition associated with the workflow definition to extract, from at least one data source, data defined by a data definition associated with the workflow definition;
      (B)(2) storing the extracted data in an evidence sheet; and
      (B)(3) applying, to the extracted data, steps defined by a workflow process definition associated with the workflow definition to generate first workflow output.

2. The method of claim 1, wherein (B) further comprises:
   (B)(4) extracting additional data defined by the data definition from the at least one data source;
   (B)(5) in response to the additional data, modifying the steps defined by the workflow process definition of the workflow definition; and
   (B)(6) applying the modified steps to the additional data to generate second workflow output.

3. The method of claim 1, wherein the at least one data source comprises at least one unstructured data source.

4. The method of claim 3, wherein (B)(1) further comprises using the process defined by the data extraction process definition associated with the workflow definition to extract, from a second data source comprising at least one structured data source, data defined by the data definition associated with the workflow definition.

5. The method of claim 1, wherein the at least one data source comprises at least one structured data source.

6. The method of claim 1, further comprising repeating (B) automatically.

7. A non-transitory computer-readable medium having computer program instructions stored thereon, wherein the computer program instructions are executable by at least one computer processor to perform a method, the method comprising:
- (A) determining that a trigger condition defined by a trigger condition definition of a workflow definition has been satisfied;
- (B) in response to the determination in (A):
  - (B)(1) using a process defined by a data extraction process definition associated with the workflow definition to extract, from at least one data source, data defined by a data definition associated with the workflow definition;
  - (B)(2) storing the extracted data in an evidence sheet; and
  - (B)(3) applying, to the extracted data, steps defined by a workflow process definition associated with the workflow definition to generate first workflow output.

8. The non-transitory computer-readable medium of claim 7, wherein (B) further comprises:
- (B)(4) extracting additional data defined by the data definition from the at least one data source;
- (B)(5) in response to the additional data, modifying the steps defined by the workflow process definition of the workflow definition; and
- (B)(6) applying the modified steps to the additional data to generate second workflow output.

9. The non-transitory computer-readable medium of claim 7, wherein the at least one data source comprises at least one unstructured data source.

10. The non-transitory computer-readable medium of claim 9, wherein (B)(1) further comprises using the process defined by the data extraction process definition associated with the workflow definition to extract, from a second data source comprising at least one structured data source, data defined by the data definition associated with the workflow definition.

11. The non-transitory computer-readable medium of claim 7, wherein the at least one data source comprises at least one structured data source.

12. The non-transitory computer-readable medium of claim 7, wherein the method further comprises repeating (B) automatically.

* * * * *